United States Patent [19]

Isshiki et al.

[11] 4,381,221
[45] Apr. 26, 1983

[54] PROCESS FOR RECOVERING A REACTION PRODUCT WHILE PREVENTING DECOMPOSITION OF THE CATALYST

[75] Inventors: Tomiya Isshiki, Tokyo; Hisashi Yoshino, Matsudo; Kaoru Tsuyuki, Tokyo, all of Japan

[73] Assignee: Mitsubishi Gas Chemical Company, Inc., Tokyo, Japan

[21] Appl. No.: 292,924

[22] Filed: Aug. 14, 1981

Related U.S. Application Data

[63] Continuation of Ser. No. 136,484, Apr. 2, 1980, abandoned.

[30] Foreign Application Priority Data

Apr. 3, 1979 [JP] Japan .................................. 54-39920

[51] Int. Cl.³ .............................................. B01D 3/34
[52] U.S. Cl. ........................................ 203/6; 203/34; 203/61; 562/519

[58] Field of Search ................ 260/419, 428; 560/248; 562/519, 607; 252/411, 441; 203/6, 34, 50, 57, 203/61

[56] References Cited

U.S. PATENT DOCUMENTS 4,039,395 8/1977 Eby ...................................... 562/519
4,102,922 7/1978 Price ................................... 562/519

*Primary Examiner*—Frank Sever
*Attorney, Agent, or Firm*—Wenderoth, Lind & Ponack

[57] ABSTRACT

In a process for recovering an aliphatic carboxylic acid and/or an ester thereof by distilling a liquid mixture containing the aliphatic carboxylic acid and/or the ester thereof and a catalyst of a metal of Group VIII of the periodic table of elements, the improvement wherein the distillation is carried out in the presence of carbon monoxide at a partial pressure of at least 0.01 kg/cm² (absolute) in the distillation system to prevent the decomposition of said catalyst.

4 Claims, No Drawings

PROCESS FOR RECOVERING A REACTION PRODUCT WHILE PREVENTING DECOMPOSITION OF THE CATALYST

This application is a continuation of Ser. No. 136,484, filed Apr. 2, 1980 now abandoned.

This invention relates to a process for recovering an aliphatic carboxylic acid or its ester by distilling the reaction mixture, which is obtained by carbonylation reaction for production of said aliphatic carboxylic acid or its ester in the presence of a catalyst comprising a metal of Group VIII of the periodic table, while preventing decomposition of the catalyst in the reaction mixture.

The process for producing a carboxylic acid or its ester by the carbonylation reaction of an alcohol or ether is known, especially as a process for producing acetic acid from methanol and carbon monoxide. We have filed applications for patents concerning a process wherein in the above reaction an aliphatic carboxylic acid aryl ester is caused to be present as a solvent and a process for producing an aliphatic acid by reacting a phenol and an aliphatic carboxylic acid ester or an ether with carbon monoxide (see German OLS 2,846,709 and 2,847,241). The reaction products of these reactions are liquid mixtures containing an aliphatic carboxylic acid, its ester and a catalyst of a metal of Group VIII of the periodic table of elements. It is the usual practice to distill the intended aliphatic carboxylic acid or its ester from the mixture and to recover the catalyst from the residual liquid. However, when these reaction liquids are heated in performing the distillation, the metal catalyst decomposes and separates out. Hence, even though the catalyst is recycled as it is to the reaction system, it is no longer able to function as a catalyst in the carbonylation reaction. Furthermore, a complicated operation is required in the treatment for regenerating the catalyst.

The object of this invention is therefore to overcome these drawbacks of the conventional processes and to provide a method which will enable the distillation and recovery of the resulting carboxylic acid or its ester without decomposition or separation of the metal catalyst and will also enable the reuse of the liquid containing the metal catalyst by recycling it to the reaction system where the carbonylation reaction is being carried out.

The foregoing object of the invention can be achieved by the method of the present invention which comprises causing carbon monoxide to be present in the distillation system at a partial pressure of at least 0.01 kg/cm$^2$ (absolute) in carrying out the distillation and recovery of the aliphatic carboxylic acid and/or its ester by distilling the liquid mixture containing the aliphatic carboxylic acid and/or its ester and the Group VIII metal catalyst.

In the instant invention a reaction product obtained by reacting, say an alcohol or ether, with carbon monoxide in the presence of a Group VIII metal catalyst and an iodine-type promoter can be used as the liquid mixture containing the aliphatic carboxylic acid and/or its ester and the Group VIII metal catalyst, as described in German OLS 2,847,241. Usable as the alcohols and ethers in this case are aliphatic alcohols of 1–20 carbon atoms, aliphatic ethers of 2–30 carbon atoms, the aromatic alcohols of 7–20 carbon atoms and the aromatic ethers of 7–30 carbon atoms.

As the catalyst of a metal of Group VIII of the periodic table, included are any of the compounds of any metal of any valency selected from the group consisting of iron, cobalt, nickel, ruthenium, rhodium, palladium, osnium, iridium and platinum. These compounds are used in an amount ranging from $10^{-6}$–1 mole, and preferably $10^{-4}$–$10^{-1}$ mole, per liter of the total of the starting material and the solvent.

As the promotor, usable are any of the compounds containing the iodine atom. Examples are $I_2$, $KI_3$, HI, $CH_3I$, $C_2H_5I$, $C_3H_7I$, $C_4H_9I$, $CH_2I_2$, $C_2H_4I_2$, $CHI_3$, $CH_3COI$, $C_2H_5CCI$, NaI, KI, LiI and $CaI_2$. The iodine atom is used in an amount of $10^{-6}$–20 moles, preferably $10^{-4}$–10 moles, based on the atom, per liter of the total of the starting material and the solvent.

For carrying out the reaction still more conveniently, an organic promotor may also be added. Usable as the organic promotor are a wide variety of the organic compounds of trivalent nitrogen, phosphorus, arsenic and antimony. Examples are trimethylamine, diethylamine, methyldiethylamine, tributylamine, aniline, N,N-dimethylaniline, N,N-dimethylacetamide, N-methyl-N-phenylacetamide, pyridine, picoline, lutidine, hydroxyquinoline, imidazole, acetonitrile, propionitrile, adiponitrile, benzonitrile, ammonium acetate, trimethylphosphine, tributylphosphine, diphenylphosphine, triphenylphosphine, methyldiphenylphosphine, triphenylarsine and triphenylstibine. And an inorganic promotor such as phosphoric acid may also be used. These compounds are used in an amount of $10^{-6}$–10 moles, and preferably $10^{-4}$–5 moles, per liter of the total of the starting material and the solvent.

On the other hand, usable as the reaction solvent are the aliphatic carboxylic acid aryl esters of the formula

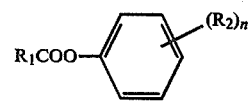

wherein $R_1$ is hydrogen or an alkyl group or alkenyl group of 1–4 carbon atoms, $R_2$ is hydrogen, alkyl, aryl, alkenyl, hydroxymethyl, acyl, acyloxy, carboxy, hydroxy, halogen, sulfonic acid, nitro, nitroso, amine, acid amide or cyano group, and two or more $R_2$ groups may be the same or different, and $R_2$ groups may be bonded to each other to form a penta- or hexa-carbocyclic or heterocyclic ring, and n is an integer from 1 to 5. When $R_2$ is a nitro group or sulfonic acid group, n is 1–2.

As examples of the aforementioned reaction solvent, there can be mentioned phenyl formate, phenyl acetate, phenyl propionate, phenyl butyrate, tolyl acetate, xylyl acetate, mesityl acetate, cumenyl acetate, ethylphenyl acetate, chlorophenyl acetate, nitrophenyl acetate, nitrosophenyl acetate, aminophenyl acetate, cyanophenyl acetate, diacetoxybenzene and naphthyl acetate. Further, such solvents that are compatible with these solvents can be mixed with these solvents. The amount of aliphatic carboxylic acid aryl ester can be used over a wide range, but it is usually used in an amount of at least 0.5, and preferably at least 1.0 mole, as phenoxy groups, per mole of the alkyl groups of the starting alcohol or ether.

The method of the present invention can also be used in the case where an aliphatic carboxylic acid or its ester is to be distilled and recovered from a reaction product liquid obtained by reacting a phenol and an aliphatic carboxylic acid ester or ether with carbon monoxide in the presence of a Group VIII metal catalyst and an iodine-type promotor as described in German OLS 2846709.

The phenols used in the foregoing reaction are those of 6–30 carbon atoms shown by the following general formula

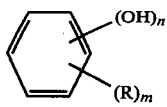

wherein n is an integer from 1 to 6, and m is an integer from 0 to 5, with the proviso that n+m=6; and R is hydrogen, alkyl, aryl, alkenyl, hydroxymethyl, acyl, acyloxy, carboxy, halogen, sulfonic acid, nitro, nitroso, amino, acid amide or cyano group, and two or more R groups may be the same or different, and R groups may be bonded to each other to form a penta-or hexa-carbocyclic or hetero-cyclic ring. When R is a nitro group or sulfonic acid group, n is 2 or less. Examples of these phenols include phenol, cresol, xylenol, trimethylphenol, tetramethylphenol, pentamethylphenol, ethylphenol, propylphenol, thymol, caruacrol, butylphenol, amylphenol, octylphenol, methylbutylphenol, diethylphenol, catechol, resorcinol, hydroquinone, dihydroxytoluene, hexylresorcinol, pyrogallol, phloroglucinol, chlorophenol, bromophenol, nitrophenol, nitrosophenol, aminophenol, N,N-dimethylaminophenol, N-methyl-N-acetylphenol, acetylphenol, formylphenol, cyanophenol, phenolsulfonic acid, methylolphenol, phenylphenol, naphthol, dihydronaphthol, tetrahydronaphthol, dihydroxynaphthalene, anthrahydroquinone, methylanthrahydroquinone, ethylanthrahydroquinone, amylanthrahydroquinone, alizarin and hydroxyquinoline.

Conveniently usable as the aliphatic carboxylic acid esters are the esters of an aliphatic carboxylic acid of 1–5 carbon atoms and an alcohol of 1–4 carbon atoms. Examples include methyl formate, propyl formate, methyl acetate, ethyl acetate, butyl acetate, methyl propionate, ethyl propionate, methyl butyrate, propyl butyrate, methyl valerate, dimethyl oxalate, diethyl oxalate and dimethyl succinate.

Conveniently usable as the aliphatic ethers are the ethers of 2–8 carbon atoms, examples of which are dimethyl ether, diethyl ether, methyl ethyl ether, dipropyl ether and dibutyl ether.

The proportion in which the phenols and the aliphatic carboxylic acid esters or aliphatic ethers are mixed can vary over a wide range, but usually the phenols are used in an amount of, based on the phenoxy group, 0.001–1000 moles, and preferably 0.01–100 moles, more preferably 0.1–10 moles, per mole of the carboxy or alkoxy group.

Since the phenols, aliphatic carboxylic acid esters and aliphatic ethers, the starting materials, and the carboxylic acid and carboxylic acid aryl esters, the reaction products, function as solvents, there is no particular need to use other solvents, but the various organic acids, ketones, hydrocarbons and inorganic acid esters can also be added if desired. The carboxylic acid aryl ester, the product, is identical to the solvent that is used in reacting the alcohol or ether with carbon monoxide, and it exhibits an especially desirable action in the reaction when used as a solvent. Furthermore, the Group VIII metal catalyst, promotor and organic promotor used in reacting the phenol with an aliphatic carboxylic acid ester or ether and carbon monoxide may be exactly the same as those used in reacting the alcohol or ether with carbon monoxide.

In recovering the carboxylic acid or its esters by distillation of the thus obtained reaction product liquid resulting from the carbonylation reaction, the decomposition and separation of the Group VIII metal catalyst from the residual liquid can be prevented by carrying out said distillation in the presence of carbon monoxide. The carbon monoxide used in this invention may, of course, be pure carbon monoxide, but it may also be those gases containing hydrogen, nitrogen and carbon dioxide in addition to carbon monoxide. Hence, it is possible to use synthesis gas and blast furnace gas. However, when a large quantity of oxygen is contained, not only is the separation of the catalyst accelerated, but also hazards from the operational standpoint are involved since the explosion limit of carbon monoxide and oxygen extends over a wide range. Therefore, it is of utmost importance to ensure that oxygen does not get mixed in.

While the amount of carbon monoxide caused to be present in the distillation zone varies depending upon say the distillation temperature and the amount of catalyst present, it usually is an amount corresponding to a partial pressure of the carbon monoxide in the distillation zone of at least 0.01 kg/cm$^2$ (absolute), and preferably at least 0.05 kg/cm$^2$ (absolute). As a result of having thus maintained a carbon monoxide atmosphere in the distillation zone, the carbonylation reaction product liquid containing the metal catalyst is brought into contact with carbon monoxide to prevent the decomposition and separation of the catalyst.

As the carbon monoxide present in the distillation zone is discharged from the distillation zone along with the distillate, it is necessary to replenish the carbon monoxide in an amount corresponding to that discharged.

The carbon monoxide in this invention functions to prevent the decomposition and separation of the catalyst and to keep it in solution in the liquid. Since the carbon monoxide is not consumed as a result of the reaction, it is recovered from the reaction product liquid after the distilled components such as the carboxylic acid and its ester have been condensed at the condenser after leaving the distillation zone. The recovered carbon monoxide is recycled to the carbonylation reaction and again used to contact the carbonylation reaction product liquid. On the other hand, the catalyst in the residual liquid is discharged from the bottom of the distillation zone in solution and is again used as catalyst in the carbonylation reaction.

While it is possible to vary the pressure used in the distillation over a wide range, nearly normal atmospheric pressure is preferred. When the pressure is high, the boiling point rises and the distillation temperature inevitably becomes high, with the consequence that the separation of the catalyst is accelerated. On the other hand, when the pressure is low, the boiling point falls, and it becomes necessary to lower the cooling temperature of the distillate, with the consequence that additional equipment such as a refrigerator is needed.

The temperature of distillation is determined by the amount of carboxylic acid or its ester to be distilled, but if the temperature is too high, the amount of carbon monoxide contacted increases and, at times, there is the possibility of the decomposition of the catalyst. Hence, it is advisable to carry out the distillation at a temperature lower than the boiling point of the highest boiling component contained in the reaction product liquid at the pressure at which the distillation is performed.

The method of this invention can be carried out by not only a batchwise distillation process but a continuous distillation process as well.

In the following examples, the catalyst dissolved rate denotes the percentage of the amount of the catalyst metal that remains dissolved in the distillation bottoms liquid based on the amount of the catalyst metal that had been in solution in the reaction product liquid. On the other hand, the composition of the starting materials is shown on a weight percent basis.

PREPARATION OF CARBOXYLIC ACIDS OR THEIR ESTERS

Preparation Experiment A

A liquid having the composition of 9.9% methanol, 50.2% phenyl acetate, 27.2% acetic acid, 0.11% rhodium chloride trihydrate, 12.4% methyl iodide and 0.2% 2,6-lutidine was continuously charged to a 500-ml autoclave equipped with an agitator, and the reaction was carried out at 200° C. and a carbon monoxide pressure of 20 kg/cm$^2$ gauge (total pressure of 30 kg/cm$^2$ gauge) with a residence time of 20 minutes. After cooling, the reaction product was withdrawn from the bottom of the autoclave and used in Examples 1 and 2 and Comparative Example 1.

Preparation Experiment B

A liquid having a composition of 9.1% methanol, 46.5% phenyl acetate, 27.9% acetic acid, 0.12% rhodium chloride trihydrate, 12.6% methyl iodide and 3.7% phosphoric acid was continuously charged to a 500-ml autoclave equipped with an agitator and reacted at 200° C. and a carbon monoxide pressure of 20 kg/cm$^2$ gauge (total pressure of 30 kg/cm$^2$ gauge) with a residence time of 20 minutes. The reaction product liquid was then withdrawn from the bottom of the autoclave and used in Examples 3 and 4 and Comparative Example 2.

Preparation Experiment C

A 300-ml autoclave equipped with an agitator was charged with 16 g of methanol, 81.6 g of phenyl acetate, 0.5 g of iridium chloride, 14.2 g of methyl iodide and 1.8 g of triphenylphosphine, and the reaction was carried out at 180° C. and a carbon monoxide pressure of 30 kg/cm$^2$ gauge (total pressure of 40 kg/cm$^2$ gauge). The half-period value was 200 minutes, and the acetic acid yield was 95.3%. This reaction was repeated several times, and the resulting reaction product liquids were collected and used in Example 5. The half-period value means the time required for absorbing 50% of theoretical amount of carbon monoxide.

Preparation Experiment D

Experiment C was repeated but using ruthenium chloride trihydrate instead of iridium chloride. The resulting product was used in Example 6.

Preparation Experiment E

A 300-ml autoclave equipped with an agitator was charged with 23 g of ethanol, 90 g of phenyl propionate, 0.335 g of rhodium chloride, trihydrate, 39 g of ethyl iodide and 0.8 g of diethylamine, and the reaction was carried out at 180° C. and a carbon monoxide pressure of 30 kg/cm$^2$ gauge (total pressure of 35 kg/cm$^2$ gauge). The half-period value was 110 minutes, and the yield of propionic acid was 90.5%. This reaction was repeated several times, and the resulting reaction product liquids were collected and used in Example 7.

Preparation Experiment F

A 300-ml autoclave equipped with an agitator was charged with 16 g of methanol, 81.6 g of phenyl acetate, 4.8 g of acetic acid, 0.9 g of palladium chloride, 29.4 g of calcium iodide and 2.9 g of triphenylphosphine, and the reaction was carried out at 200° C. and a carbon monoxide pressure of 30 kg/cm$^3$ gauge (total pressure of 40 kg/cm$^2$ gauge). The yield of acetic acid was 96.0%. This reaction was repeated twice, and the resulting reaction product liquids were collected and used in Example 8.

Preparation Experiment G

The reactor used in Experiment A was continuously charged with a liquid composed of 25.9% of methyl acetate, 40.1% of phenol, 21.8% of acetic acid, 0.42% of rhodium chloride trihydrate, 11.6% of methyl iodide and 0.21% of 2,6-lutidine, and the reaction was carried out at 200° C. and a carbon monoxide pressure of 20 kg/cm$^2$ gauge (total pressure of 30 kg/cm$^2$ gauge) with a residence time of 20 minutes. The reaction product liquid was collected and used in Examples 9, 10 and 15 and Comparative Example 3.

Preparation Experiment H

The reactor used in Experiment A was continuously charged with a liquid having the composition of 25.1% methyl acetate, 38.9% phenol, 19.5% acetic acid, 0.13% rhodium chloride trihydrate, 12.4% methyl iodide and 3.9% phosphoric acid, following which the reaction was carried out at 200° C. and a carbon monoxide pressure of 20 kg/cm$^2$ gauge (total pressure of 30 kg/cm$^2$ gauge) with a residence time of 20 minutes. The resulting reaction product liquid was collected and used in Examples 11 and 12 and Comparative Example 4.

Preparation Example I

A 300-ml autoclave equipped with an agitator was charged with 59.2 g of methyl acetate, 104 g of p-cresol, 1.8 g of palladium chloride, 31.5 g of methyl iodide and 5.8 g of triphenylphosphine, and the reaction was carried out at 195° C. and a carbon monoxide pressure of 28 kg/cm$^2$ gauge (total pressure of 38 kg/cm$^2$ gauge). The yields of acetic acid and phenyl acetate were 95.8% and 95.6%, respectively. The reaction was repeated several times, and the resulting reaction product liquids were collected and used in Example 13.

Preparation Experiment J

A 300-ml autoclave equipped with an agitator was charged with 23 g of dimethyl ether, 56.4 g of phenyl, 30 g of acetic acid, 1.0 g of RhCl(CO)(P$\phi_3$)$_2$ and 14.2 g of methyl iodide, following which the reaction was carried out at 190° C. and a carbon monoxide pressure of 30 kg/cm$^2$ gauge (total pressure of 50 kg/cm$^2$ gauge). The yields of acetic acid and phenyl acetate were 97.3% and 97.2%, respectively. The reaction was repeated several times, and the resulting reaction product liquids were collected and used in Example 14.

Examples 1-7 and Comparative Examples 1-2

The liquids obtained in Preparation Experiments A-E were charged to the distillation apparatus at a flow rate of 400 grams per hour and continuously distilled with the results shown in Table 1.

Example 8

The reaction product liquid (200 g) obtained in Preparation Experiment F was taken in a round-bottom flask equipped with a capillary and a distillate condenser and distilled at 400 mm Hg. Carbon monoxide was fed via the capillary during the distillation operation. The results obtained are shown in Table 1.

Examples 9-10 and Comparative Example 3

The continuous distillation of the reaction product liquid obtained in Preparation Experiment G was carried out by continuously introducing the liquid to a distillation apparatus at a rate of 420 grams per hour via a preheater. The distillation conditions and the results obtained are shown in Table 1.

Examples 11-12 and Comparative Example 4

The liquid obtained in Preparation Experiment H was introduced into a distillation apparatus at a flow rate of 271 grams per hour via a preheater and continuously distilled. The distillation conditions and the results obtained are shown in Table 1.

Example 13

The reaction product liquid obtained in Preparation Experiment I was introduced into a distillation apparatus at a flow rate of 270 grams per hour via a preheater and continuously distilled. The distillation conditions and the results obtained are shown in Table 1.

Example 14

The reaction product liquid obtained in Preparation Experiment J was continuously distilled by introducing it into a distillation apparatus at a rate of 270 grams per hour via a preheater. The distillation conditions and the results obtained are shown in Table 1.

Example 15

A 500-ml round-bottom flask fitted with a capillary, a distillate condenser and a suction means was charged with 300 g of the reaction product liquid obtained in Preparation Experiment G, and the flask was purged with carbon monoxide. The flask was then heated and, after reducing the pressure inside the flask to 500 mm Hg with the suction means, carbon monoxide was fed via the capillary. On distillation of about 100 g of the liquid, there was obtained a fraction whose principal components were methyl iodide, methyl acetate and acetic acid. The results obtained are shown in Table 1.

TABLE 1 - 1

| | Composition of reaction product liquid | | Example or Comp. Ex. | Distillation temperature (°C.) | Circulating gas | | Overhead vapor | | |
|---|---|---|---|---|---|---|---|---|---|
| | | | | | Class | Flow rate (litr/hr) | Amount distilled (g/hr) | Concentration of carboxylic acid (%) | |
| A | acetic acid | 38.5% | Example 1 | 111 | CO | 35 | 168 | acetic acid | 52.4 |
| | phenyl acetate | 37.2% | | | | | | | |
| | methyl acetate | 5.5% | Example 2 | 112 | CO | 65 | 183 | acetic acid | 54.5 |
| | phenol | 7.0% | Comp. Ex 1 | 111 | air | 48 | 169 | acetic acid | 52.7 |
| | Rh | 422 ppm | | | | | | | |
| | methyl iodide | 11.7% | | | | | | | |
| | 2,6-lutidine | 0.2% | | | | | | | |
| B | acetic acid | 38.6% | Example 3 | 107 | CO | 32 | 134 | acetic acid | 51.3 |
| | phenyl acetate | 35.1% | | | | | | | |
| | methyl acetate | 4.8% | Example 4 | 105 | CO | 67 | 152 | acetic acid | 52.3 |
| | phenol | 6.1% | | | | | | | |
| | Rh | 439 ppm | Comp. Ex 2 | 105 | air | 60 | 154 | acetic acid | 52.5 |
| | methyl iodide | 11.9% | | | | | | | |
| | phosphoric acid | 3.5% | | | | | | | |
| C | acetic acid | 22.4% | Example 5 | 113 | CO | 45 | 148 | acetic acid | 34.1 |
| | phenyl acetate | 61.5% | | | | | | | |
| | methyl acetate | 1.3% | | | | | | | |
| | phenol | 1.7% | | | | | | | |
| | Ir | 2509 ppm | | | | | | | |
| | methyl iodide | 11.1% | | | | | | | |
| | triphenylphosphine | 1.4% | | | | | | | |
| D | acetic acid | 21.7% | Example 6 | 110 | CO | 43 | 151 | acetic acid | 33.6 |
| | phenyl acetate | 59.9% | | | | | | | |
| | methyl acetate | 2.6% | | | | | | | |
| | phenol | 3.3% | | | | | | | |
| | Ru | 1545 ppm | | | | | | | |
| | methyl iodide | 11.3% | | | | | | | |
| | triphenylphosphine | 2.6% | | | | | | | |
| E | propionic acid | 20.2% | Example 7 | 120 | CO | 65 | 137 | propionic acid | 23.0 |
| | phenyl propionate | 50.0% | | | | | | | |

TABLE 1 - 1-continued

| | Composition of reaction product liquid | | Example or Comp. Ex. | Distillation temperature (°C.) | Circulating gas Class | Circulating gas Flow rate (litr/hr) | Overhead vapor Amount distilled (g/hr) | Overhead vapor Concentration of carboxylic acid (%) | |
|---|---|---|---|---|---|---|---|---|---|
| | ethyl propionate | 2.9% | | | | | | | |
| | phenol | 2.7% | | | | | | | |
| | Rh | 782 ppm | | | | | | | |
| | ethyl iodide | 23.5% | | | | | | | |
| | diethylamine | 0.4% | | | | | | | |
| F | acetic acid | 40.0% | Example 8 | 116 | CO | minute quantity | 43 | acetic acid | 81.1 |
| | methyl acetate | 0.8% | | | | | | | |
| | phenyl acetate | 41.0% | | | | | | | |
| | phenol | 1.0% | | | | | | | |
| | Pd | 2800 ppm | | | | | | | |
| | calcium iodide | 15.3% | | | | | | | |
| | triphenylphosphine | 1.5% | | | | | | | |
| G | acetic acid | 35.7% | Example 9 | 111 | CO | 41 | 176 | acetic acid | 52.4 |
| | methyl acetate | 5.5% | Example 10 | 112 | CO | 71 | 193 | acetic acid | 54.4 |
| | phenyl acetate | 34.5% | Comp. Ex 3 | 111 | $N_2$ | 48 | 175 | acetic acid | 52.7 |
| | phenol | 13.5% | Example 15 | 126 | CO | minute quantity | 100 | acetic acid | 51.6 |
| | Rh | 422 ppm | | | | | | | |
| | methyl iodide | 10.8% | | | | | | | |
| | 2,6-lutidine | 0.17% | | | | | | | |
| H | acetic acid | 35.2% | | | | | | | |
| | methyl acetate | 4.8% | Example 11 | 105 | CO | 46 | 103 | acetic acid | 52.3 |
| | phenyl acetate | 32.0% | Example 12 | 107 | CO | 22 | 91 | acetic acid | 51.3 |
| | phenol | 12.3% | Comp. Ex 4 | 105 | air | 39 | 105 | acetic acid | 52.5 |
| | Rh | 439 ppm | | | | | | | |
| | methyl iodide | 10.9% | | | | | | | |
| | phosphoric acid | 3.5% | | | | | | | |
| I | acetic acid | 20.6% | | | | | | | |
| | methyl acetate | 1.1% | Example 13 | 110 | CO | 47 | 54 | acetic acid | 38.6 |
| | p-tolyl acetate | 51.3% | | | | | | | |
| | p-cresol | 9.6% | | | | | | | |
| | Pd | 4800 ppm | | | | | | | |
| | methyl iodide | 14.1% | | | | | | | |
| | triphenylphosphine | 2.6% | | | | | | | |
| J | acetic acid | 39.0% | | | | | | | |
| | phenyl acetate | 43.5% | Example 14 | 113 | CO | 42 | 115 | acetic acid | 57.2 |
| | dimethyl ether | 0.4% | | | | | | | |
| | phenol | 7.0% | | | | | | | |
| | Rh | 980 ppm | | | | | | | |
| | methyl iodide | 9.4% | | | | | | | |
| | triphenylphosphine | 0.5% | | | | | | | |

TABLE 1 - 2

| | Composition of reaction product liquid | | Example or Comp. Ex. | Bottoms liquid Amount (g/hr) | Bottoms liquid Catalyst dissolved rate (%) | Pressure Total [kg/cm² (abs)] | Pressure CO partial [kg/cm² (abs)] |
|---|---|---|---|---|---|---|---|
| A | acetic acid | 38.5% | Example 1 | 232 | 100.0 | 1 | 0.41 |
| | phenyl acetate | 37.2% | Example 2 | 217 | 99.3 | 1 | 0.54 |
| | methyl acetate | 5.5% | Comp. Ex. 1 | 231 | 4.7 | 1 | 0 |
| | phenol | 7.0% | | | | | |
| | Rh | 422 ppm | | | | | |
| | methyl iodide | 11.7% | | | | | |
| | 2,6-lutidine | 0.2% | | | | | |
| B | acetic acid | 38.6% | Example 3 | 266 | 97.8 | 1 | 0.44 |
| | phenyl acetate | 35.1% | Example 4 | 248 | 100.0 | 1 | 0.59 |
| | methyl acetate | 4.8% | Comp. Ex. 2 | 246 | 49.8 | 1 | 0 |
| | phenol | 6.1% | | | | | |
| | Rh | 439 ppm | | | | | |
| | methyl iodide | 11.9% | | | | | |
| | phosphoric acid | 3.5% | | | | | |

TABLE 1 - 2-continued

| Composition of reaction product liquid | | Example or Comp. Ex. | Bottoms liquid Amount (g/hr) | Catalyst dissolved rate (%) | Pressure Total [kg/cm² (abs)] | CO partial [kg/cm² (abs)] |
|---|---|---|---|---|---|---|
| C | acetic acid 22.4% | | | | | |
| | phenyl acetate 61.5% | Example 5 | 252 | 98.8 | 1 | 0.56 |
| | methyl acetate 1.3% | | | | | |
| | phenol 1.7% | | | | | |
| | Ir 2509 ppm | | | | | |
| | methyl iodide 11.1% | | | | | |
| | triphenylphosphine 1.4% | | | | | |
| D | acetic acid 21.7% | | | | | |
| | phenyl acetate 59.9% | Example 6 | 249 | 99.1 | 1 | 0.54 |
| | methyl acetate 2.6% | | | | | |
| | phenol 3.3% | | | | | |
| | Ru 1545 ppm | | | | | |
| | methyl iodide 11.3% | | | | | |
| | triphenylphosphine 2.6% | | | | | |
| E | propionic acid 20.2% | | | | | |
| | phenyl propionate 50.0% | Example 7 | 263 | 95.4 | 1 | 0.72 |
| | ethyl propionate 2.9% | | | | | |
| | phenol 2.7% | | | | | |
| | Rh 782 ppm | | | | | |
| | ethyl iodide 23.5% | | | | | |
| | diethylamine 0.4% | | | | | |
| F | acetic acid 40.0% | | | | | |
| | methyl acetate 0.8% | Example 8 | 157 | 99.1 | 0.53 | 0.10 |
| | phenyl acetate 41.0% | | | | | |
| | phenol 1.0% | | | | | |
| | Pd 2800 ppm | | | | | |
| | calcium iodide 15.3% | | | | | |
| | triphenylphosphine 1.5% | | | | | |
| G | acetic acid 35.7% | | | | | |
| | methyl acetate 5.5% | Example 9 | 244 | 100.0 | 1 | 0.44 |
| | phenyl acetate 34.5% | Example 10 | 227 | 99.2 | 1 | 0.55 |
| | phenol 13.5% | Comp. Ex. 3 | 245 | 4.7 | 1 | 0 |
| | Rh 422 ppm | Example 15 | 200 | 99.5 | 0.66 | 0.10 |
| | methyl iodide 10.8% | | | | | |
| | 2,6-lutidine 0.17% | | | | | |
| H | acetic acid 35.2% | | | | | |
| | methyl acetate 4.8% | Example 11 | 168 | 100.0 | 1 | 0.60 |
| | phenyl acetate 32.0% | Example 12 | 180 | 97.8 | 1 | 0.44 |
| | phenol 12.3% | Comp. Ex. 4 | 166 | 48.2 | 1 | 0 |
| | Rh 439 ppm | | | | | |
| | methyl iodide 10.9% | | | | | |
| | phosphoric acid 3.5% | | | | | |
| I | acetic acid 20.6% | | | | | |
| | methyl acetate 1.1% | Example 13 | 216 | 98.7 | 1 | 0.78 |
| | p-tolyl acetate 51.3% | | | | | |
| | p-cresol 9.6% | | | | | |
| | Pd 4800 ppm | | | | | |
| | methyl iodide 14.1% | | | | | |
| | triphenylphosphine 2.6% | | | | | |
| J | acetic acid 39.0% | | | | | |
| | phenyl acetate 43.5% | Example 14 | 155 | 99.8 | 1 | 0.55 |
| | dimethyl ether 0.4% | | | | | |
| | phenol 7.0% | | | | | |
| | Rh 980 ppm | | | | | |
| | methyl iodide 9.4% | | | | | |
| | triphenylphosphine 0.5% | | | | | |

Example 16

A distillation apparatus was connected through a valve to the withdrawal port at the bottom of the 500-ml autoclave equipped with an agitator used in Preparation Experiment A. A liquid consisting of 5.8% of methanol, 10.1% of methyl acetate, 25.9% of acetic acid, 6.4% of phenol, 37.6% of phenyl acetate, 12.8% of methyl iodide, 0.05% of rhodium and 1.0% of triphenyl-phosphine was charged to the autoclave at a rate of 1,154 grams per hour. Concurrently, carbon monoxide was introduced under a pressure of 20 kg/cm² gauge. While maintaining the total pressure at 30 kg/cm² gauge, the reaction was carried out continuously at 200° C. The reaction product liquid containing 35.1% of acetic acid was withdrawn from the bottom of the autoclave and sent to the distillation apparatus at an hourly rate of 1,219 grams and distilled. The amount distilled per hour was 476 grams, and the concentration of acetic acid was 44.7%. The partial pressure of carbon monoxide in the distillation zone was 0.02 kg/cm² (abs), and the catalyst dissolved rate was 99.9%.

What is claimed is:

1. In a process for recovering an aliphatic carboxylic acid and/or an ester thereof by distilling a liquid mixture containing the aliphatic carboxylic acid and/or the ester thereof and a catalyst of a metal of Group VIII of the periodic table of elements, the improvement wherein carbon monoxide is introduced into the distillation system to carry out the distillation in the presence of carbon monoxide at a partial pressure of at least 0.05 kg/cm$^2$ (absolute) in the distillation system to prevent the decomposition of said catalyst, there being no catalyst removed from said liquid mixture to be distilled, the amount of said catalyst in said liquid mixture to be distilled being $10^{-4}$ to $10^{-1}$ mole per liter of the total of the starting material and solvent used to obtain said liquid mixture.

2. The process of claim 1 wherein said liquid mixture is a liquid reaction mixture obtained by reacting a phenol, an aliphatic carboxylic acid ester or an aliphatic ether, and carbon monoxide in the presence of a catalyst of a metal of Group VIII of the periodic table of elements and an iodine-type promotor.

3. The process of claim 1 wherein said liquid mixture is a liquid reaction mixture obtained by reacting an alcohol or an ether with carbon monoxide in the presence of a catalyst consisting of a compound of a metal of Group VIII of the periodic table of elements and an iodine-type promotor.

4. The process of claim 1 wherein said liquid mixture is a liquid reaction mixture obtained directly from a reaction for producing said aliphatic carboxylic acid and/or the ester thereof.

* * * * *